(12) United States Patent
Maleki et al.

(10) Patent No.: US 8,210,044 B1
(45) Date of Patent: Jul. 3, 2012

(54) COVERT LASER REMOTE SENSING AND VIBROMETRY

(75) Inventors: Lutfollah Maleki, Pasadena, CA (US); Nan Yu, Arcadia, CA (US); Andrey B. Matsko, Pasadena, CA (US); Anatoliy Savchenkov, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 891 days.

(21) Appl. No.: 12/288,011

(22) Filed: Oct. 14, 2008

Related U.S. Application Data

(60) Provisional application No. 60/998,688, filed on Oct. 12, 2007.

(51) Int. Cl.
*G01N 29/24* (2006.01)
*G01N 29/46* (2006.01)

(52) U.S. Cl. ......................................................... 73/643
(58) Field of Classification Search ...................... 73/643
See application file for complete search history.

(56) References Cited

U.S. PATENT DOCUMENTS

| | | | | |
|---|---|---|---|---|
| 4,129,041 A | * | 12/1978 | Bickel | 73/657 |
| 4,607,341 A | * | 8/1986 | Monchalin | 702/136 |
| 4,659,224 A | * | 4/1987 | Monchalin | 356/502 |
| 4,928,152 A | | 5/1990 | Gerardin | |
| 5,204,640 A | | 4/1993 | Logan, Jr. | |
| 5,220,292 A | | 6/1993 | Bianchini et al. | |
| 5,723,856 A | | 3/1998 | Yao et al. | |

(Continued)

FOREIGN PATENT DOCUMENTS
WO 01/096936 12/2001
(Continued)

OTHER PUBLICATIONS

Aguanno, M.V., et al., "Full-field laser vibrometry employing a novel CMOS-DSP camera," *Proceedings of the SPIE 5th International Conference on Vibration Measurements by Laser Techniques: Advances and Applications*, vol. 4827, pp. 123-132, May 2002.

(Continued)

*Primary Examiner* — Hezron E Williams
*Assistant Examiner* — Rose M Miller
(74) *Attorney, Agent, or Firm* — Perkins Coie LLP

(57) ABSTRACT

Designs of single-beam laser vibrometry systems and methods. For example, a method for detecting vibrations of a target based on optical sensing is provided to include operating a laser to produce a laser probe beam at a laser frequency and modulated at a modulation frequency onto a target; collecting light at or near the laser to collect light from the target while the target is being illuminated by the laser probe beam through an optical receiver aperture; using a narrow-band optical filter centered at the laser frequency to filter light collected from the optical receiver aperture to transmit light at the laser frequency while blocking light at other frequencies; using an optical detector to convert filtered light from the narrow-band optical filter to produce a receiver electrical signal; using a lock-in amplifier to detect and amplify the receiver electrical signal at the modulation frequency while rejecting signal components at other frequencies to produce an amplified receiver electrical signal; processing the amplified receiver electrical signal to extract information on vibrations of the target carried by reflected laser probe beam in the collected light; and controlling optical power of the laser probe beam at the target to follow optical power of background illumination at the target.

19 Claims, 5 Drawing Sheets

U.S. PATENT DOCUMENTS

| | | | |
|---|---|---|---|
| 5,737,085 A * | 4/1998 | Zollars et al. | 356/623 |
| 5,751,747 A | 5/1998 | Lutes et al. | |
| 5,777,778 A | 7/1998 | Yao | |
| 5,838,439 A | 11/1998 | Zang et al. | |
| 5,917,179 A | 6/1999 | Yao | |
| 5,929,430 A | 7/1999 | Yao et al. | |
| 5,985,166 A | 11/1999 | Unger et al. | |
| 6,080,586 A | 6/2000 | Baldeschwieler et al. | |
| 6,178,036 B1 | 1/2001 | Yao | |
| 6,186,004 B1 * | 2/2001 | Kaduchak et al. | 73/596 |
| 6,203,660 B1 | 3/2001 | Unger et al. | |
| 6,389,197 B1 | 5/2002 | Iltchenko et al. | |
| 6,417,957 B1 | 7/2002 | Yao | |
| 6,473,218 B1 | 10/2002 | Maleki et al. | |
| 6,476,959 B2 | 11/2002 | Yao | |
| 6,487,233 B2 | 11/2002 | Maleki et al. | |
| 6,488,861 B2 | 12/2002 | Iltchenko et al. | |
| 6,490,039 B2 | 12/2002 | Maleki et al. | |
| 6,535,328 B2 | 3/2003 | Yao | |
| 6,567,436 B1 | 5/2003 | Yao et al. | |
| 6,580,532 B1 | 6/2003 | Yao et al. | |
| 6,594,061 B2 | 7/2003 | Huang et al. | |
| 6,762,869 B2 | 7/2004 | Maleki et al. | |
| 6,795,481 B2 | 9/2004 | Maleki et al. | |
| 6,798,947 B2 | 9/2004 | Iltchenko | |
| 6,853,479 B1 | 2/2005 | Ilchenko et al. | |
| 6,871,025 B2 | 3/2005 | Maleki et al. | |
| 6,873,631 B2 | 3/2005 | Yao et al. | |
| 6,879,752 B1 | 4/2005 | Ilchenko et al. | |
| 6,901,189 B1 | 5/2005 | Savchenkov et al. | |
| 6,906,309 B2 | 6/2005 | Sayyah et al. | |
| 6,922,497 B1 | 7/2005 | Savchenkov et al. | |
| 6,928,091 B1 | 8/2005 | Maleki et al. | |
| 6,943,934 B1 | 9/2005 | Ilchenko et al. | |
| 6,987,914 B2 | 1/2006 | Savchenkov et al. | |
| 7,024,069 B2 | 4/2006 | Savchenkov et al. | |
| 7,043,117 B2 | 5/2006 | Matsko et al. | |
| 7,050,212 B2 | 5/2006 | Matsko et al. | |
| 7,061,335 B2 | 6/2006 | Maleki et al. | |
| 7,062,131 B2 | 6/2006 | Ilchenko | |
| 7,092,591 B2 | 8/2006 | Savchenkov et al. | |
| 7,133,180 B2 | 11/2006 | Ilchenko et al. | |
| 7,173,749 B2 | 2/2007 | Maleki et al. | |
| 7,184,451 B2 | 2/2007 | Ilchenko et al. | |
| 7,187,870 B2 | 3/2007 | Ilchenko et al. | |
| 7,218,662 B1 | 5/2007 | Ilchenko et al. | |
| 7,248,763 B1 | 7/2007 | Kossakovski et al. | |
| 7,260,279 B2 | 8/2007 | Gunn et al. | |
| 7,283,707 B1 | 10/2007 | Maleki et al. | |
| 7,356,214 B2 | 4/2008 | Ilchenko | |
| 7,362,927 B1 | 4/2008 | Ilchenko et al. | |
| 7,369,722 B2 | 5/2008 | Yilmaz et al. | |
| 7,389,053 B1 | 6/2008 | Ilchenko et al. | |
| 7,400,796 B1 | 7/2008 | Kossakovski et al. | |
| 7,440,651 B1 | 10/2008 | Savchenkov et al. | |
| 7,460,746 B2 | 12/2008 | Maleki et al. | |
| 7,480,425 B2 | 1/2009 | Gunn et al. | |
| 7,798,000 B1 * | 9/2010 | Murray et al. | 73/597 |
| 2001/0038651 A1 | 11/2001 | Maleki et al. | |
| 2002/0018611 A1 | 2/2002 | Maleki et al. | |
| 2002/0018617 A1 | 2/2002 | Iltchenko et al. | |
| 2002/0021765 A1 | 2/2002 | Maleki et al. | |
| 2002/0081055 A1 | 6/2002 | Painter et al. | |
| 2002/0085266 A1 | 7/2002 | Yao | |
| 2002/0097401 A1 | 7/2002 | Maleki et al. | |
| 2003/0160148 A1 | 8/2003 | Yao et al. | |
| 2004/0100675 A1 | 5/2004 | Matsko et al. | |
| 2004/0109217 A1 | 6/2004 | Maleki et al. | |
| 2004/0218880 A1 | 11/2004 | Matsko et al. | |
| 2004/0240781 A1 | 12/2004 | Savchenkov et al. | |
| 2005/0017816 A1 | 1/2005 | Ilchenko et al. | |
| 2005/0063034 A1 | 3/2005 | Maleki et al. | |
| 2005/0074200 A1 | 4/2005 | Savchenkov et al. | |
| 2005/0099634 A1 * | 5/2005 | Dubois et al. | 356/502 |
| 2005/0123306 A1 | 6/2005 | Ilchenko et al. | |
| 2005/0128566 A1 | 6/2005 | Savchenkov et al. | |
| 2005/0175358 A1 | 8/2005 | Ilchenko et al. | |
| 2005/0248823 A1 | 11/2005 | Maleki et al. | |
| 2007/0009205 A1 | 1/2007 | Maleki et al. | |
| 2007/0153289 A1 | 7/2007 | Yilmaz et al. | |
| 2008/0001062 A1 | 1/2008 | Gunn et al. | |
| 2008/0075464 A1 | 3/2008 | Maleki et al. | |
| 2008/0170235 A1 | 7/2008 | Rogers et al. | |
| 2008/0310463 A1 | 12/2008 | Maleki et al. | |
| 2009/0097516 A1 | 4/2009 | Maleki et al. | |
| 2009/0135860 A1 | 5/2009 | Maleki et al. | |
| 2009/0289198 A1 * | 11/2009 | Youngner | 250/458.1 |

FOREIGN PATENT DOCUMENTS

| | | |
|---|---|---|
| WO | 2005/038513 | 4/2005 |
| WO | 2005/055412 | 6/2005 |
| WO | 2005/067690 | 7/2005 |
| WO | 2005/122346 | 12/2005 |
| WO | 2006/076585 | 7/2006 |
| WO | 2007/143627 | 12/2007 |

OTHER PUBLICATIONS

Braginsky, V.B., et al., "Quality-Factor and Nonlinear Properties of Optical Whispering-Gallery Modes," *Physics Letters A*, 137(7, 8):393-397, May 1989.

Eliyahu, D., et al., "Low Phase Noise and Spurious Levels in Multi-Loop Opto-Electronic Oscillators," *Proceedings of the 2003 IEEE International Frequency Control Sympsoium and PDA Exhibition*, pp. 405-410, May 2003.

Eliyahu, D., et al., "Modulation Response ($S_{21}$) of the Coupled Opto-Electronic Oscillator," *Proceedings of the 2005 IEEE International Frequency Control Symposium and Exposition*, pp. 850-856, Aug. 2005.

Eliyahu, D., et al., "Tunable, Ultra-Low Phase Noise YIG Based Opto-Electronic Oscillator," *IEEE MTT-S International Microwave Symposium Digest*, 3:2185-2187, Jun. 2003.

Gorodetsky, M.L., et al., "Optical Microsphere Resonators: Optimal Coupling to High-$Q$ Whispering-Gallery Modes," *J.Opt. Soc. Am. B*, 16(1):147-154, Jan. 1999.

Gorodetsky, M.L., et al., "Rayleigh Scattering in High-$Q$ Microspheres," *J. Opt. Soc. Am. B*, 17(6):1051-1057, Jun. 2000.

Gorodetsky, M.L., et al., "Ultimate $Q$ of Optical Microsphere Resonators," *Optics Letters*, 21(7):453-455, Apr. 1996.

Hryniewicz, J.V., et al., "Higher Order Filter Response in Coupled Microring Resonators," *IEEE Photonics Technology Letters*, 12(3):320-322, Mar. 2000.

Huang, S., et al., "A 'Turnkey' Optoelectronic Oscillator with Low Acceleration Sensitivity," *2000 IEEE/EIA International Frequency Control Symposium and Exhibition*, pp. 269-279, Jun. 2000.

Ilchenko, V., et al., "Electrooptically Tunable Photonic Microresonators and Photonic Bandgap Waveguide Coupling for Micro-Optoelectronic Oscillators," *GOMACTech 2003*, Tampa, Florida, pp. 1-4.

Ilchenko, V., et al., "High-Q Microsphere Cavity for Laser Stabilization and Optoelectronic Microwave Oscillator," *Proceedings SPIE Microresonators and Whispering-Gallery Modes*, vol. 3611, pp. 190-198, Jan. 1999.

Ilchenko, V., et al., "Microsphere Integration in Active and Passive Photonics Devices," *Proc. of SPIE Laser Resonators III*, vol. 3930, pp. 154-162, Jan. 2000.

Ilchenko, V., et al., "Microtorus: A High-Finesse Microcavity with Whispering-Gallery Modes," *Optics Letters*, 26(5):256-258, Mar. 2001.

Ilchenko, V., et al., "Pigtailing the High-$Q$ Microsphere Cavity: A Simple Fiber Coupler for Optical Whispering-Gallery Modes," *Optics Letters*, 24(11):723-725, Jun. 1999.

Ilchenko, V., et al., "Sub-Micro Watt Photonic Microwave Receiver," *IEEE Photonics Technology Letters*, 14(11):1602-1604, Nov. 2002.

Ilchenko, V., et al., "Tunability and Synthetic Lineshapes in High-Q Optical Whispering Gallery Modes," *Proc. of SPIE Laser Resonators and Beam Control VI*, vol. 4969, pp. 195-206, Jan. 2003.

Ilchenko, V., et al., "Whispering-Gallery-Mode Electro-Optic Modulator and Photonic Microwave Receiver," *J. Opt. Soc. Am. B*, 20(2):333-342, Feb. 2003.

Ito, H., et al., "InP/InGaAs Uni-Travelling-Carrier Photodiode with 310 GHz Bandwidth," *Electronics Letters*, 36(21):1809-1810, Oct. 2000.

Logan, R., et al., "Stabilization of Oscillator Phase Using a Fiber-Optic Delay-Line," *IEEE 45th Annual Symposium on Frequency Control*, pp. 508-512, May 1991.

Maleki, L., "The Opto-Electronic Oscillator: Prospects for Extending the State of the Art in Reference Frequency Generation," *International Topical Meeting on Microwave Photonics*, pp. 195-198, Oct. 1998.

Matsko, A., et al., "Active Mode Locking with Whispering-Gallery Modes," *J. Opt. Soc. Am. B*, 20(11):2292-2296, Nov. 2003.

Matsko, A., et al., "Whispering-Gallery-Mode based Optoelectronic Microwave Oscillator," *Journal of Modern Optics*, 50(15-17):2523-2542, Feb. 2004.

Matsko, A., et al., "Whispering-Gallery-Mode Resonators as Frequency References. I. Fundamental Limitations," *J. Opt. Soc. Am. B*, 24(6):1324-1335, Jun. 2007.

Myers, L.E., et al., "Quasi-Phase-Matched Optical Parametric Oscillators in Bulk Periodically Poled $LiNbO_3$," *J. Opt. Soc. Am. B*, 12(11):2102-2116, Nov. 1995.

Redman, B.C., et al., "Direct-detection laser vibrometry with an amplitude-modulated ladar," *Proceedings of the SPIE Laser Radar Technology and Applications IX*, vol. 5412, pp. 218-228, Sep. 2004.

Savchenkov, A., et al., "Whispering-Gallery-Mode Resonators as Frequency References. II. Stabilization," *J. Opt. Soc. Am. B*, 24(12): 2988-2997, Dec. 2007.

Vassiliev, V.V., et al., "Narrow-Line-Width Diode Laser with a High-$Q$ Microsphere Resonator," *Optics Communications*, 158(1-6):305-312, Dec. 1998.

Yao, X.S., et al., "A Novel Photonic Oscillator," *Digest of the LEOS Summer Topical Meetings*, pp. 17-18, Aug. 1995.

Yao, X.S., et al., "A Novel Photonic Oscillator," *TDA Progress Report 42-122*, pp. 32-43, Aug. 1995.

Yao, X.S., et al., "Converting Light into Spectrally Pure Microwave Oscillation," *Optics Letters*, 21(7):483-485, Apr. 1996.

Yao, X.S., et al., "Coupled Optoelectronic Oscillators for Generating Both RF Signal and Optical Pulses," *Journal of Lightwave Technology*, 18(1):73-78, Jan. 2000.

Yao, X.S., et al., "Dual Microwave and Optical Oscillator," *Optics Letters*, 22(24):1867-1869, Dec. 1997.

Yao, X.S., et al., "Multiloop Optoelectronic Oscillator," *IEEE Journal of Quantum Electronics*, 36(1):79-84, Jan. 2000.

Yao, X.S., et al., "Optoelectronic Microwave Oscillator," *J. Opt. Soc. Am. B*, 13(8):1725-1735, Aug. 1996.

Yao, X.S., et al., "Optoelectronic Oscillator for Photonic Systems," *IEEE Journal of Quantum Electronics*, 32(7):1141-1149, Jul. 1996.

Yu, J., et al., "Compact Optoelectronic Oscillator with Ultra-Low Phase Noise Performance," *Electronics Letters*, 35(18):1554-1555, Sep. 1999.

\* cited by examiner

COVERT LASER REMOTE SENSING AND VIBROMETRY

PRIORITY CLAIM AND RELATED APPLICATIONS

This application claims the benefit of the U.S. Provisional Application No. 60/998,688 entitled "Space-born non-cooperative covert remote hearing and vibrometry" and filed Oct. 12, 2007, the disclosure of which is incorporated by reference as part of the specification of this application.

FEDERALLY SPONSORED RESEARCH OR DEVELOPMENT

The invention described herein was made in the performance of work under a NASA contract, and is subject to the provisions of Public Law 96-517 (35 USC 202) in which the Contractor has elected to retain title.

BACKGROUND

This application relates to optical sensors including optical vibrometry measurements.

Laser vibrometry measurements use two coherent laser beams from a single laser: one as a probe beam and another as a reference beam. The probe beam is directed to a target and gets reflected back to optically interfere with the reference beam to produce an interference signal. This interference signal is detected to extract the vibration information of the target which indices a Doppler shift in the reflected probe light.

DETAILED DESCRIPTION

The system in this document can be used to provide an acousto-photonic system for remote detection and analysis as well as for covert recognition of distant non-cooperative objects (targets of tactical and/or strategic importance). For example, the targets can belong to particular types of mechanical tooling operating under the roof of a factory or deep underground. The acousto-photonic system can be used for remote recognition of a fake construction such as a garage or a factory, remote recognition of fake weaponry placed on the battlefield and identification of fake launched warheads.

Figure 1:
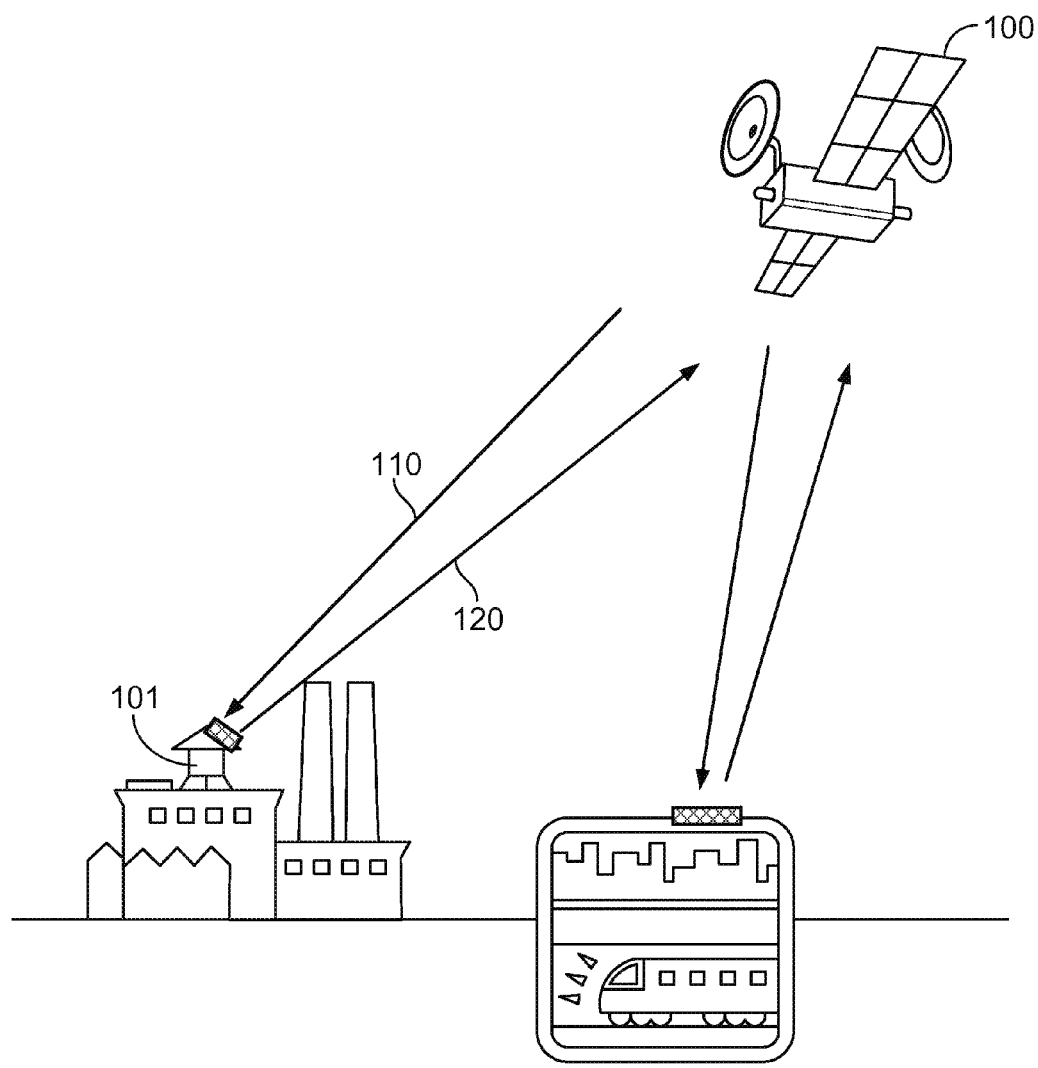
FIG. 1 shows a laser vibrometry system for remote sensing from an airborne laser system.

FIG. 1 shows one example of such a system where the laser sensing module 100 sends a single laser probe beam 110 to a target 101 and collects returned light 120 from the target. The returned light includes the backscattered or reflected probe light from the laser 100 and background light.

Our system has two distinct features:

a) The target recognition can be covert. The power of the optical carrier will always be kept below the natural illumination background to be completely unrecognizable by modern detectors. Our advanced filtering at selected optical wavelength will remove all the ambient illumination which would saturate optical detector of the vibrometer. Additional stage of the detection will include lock-in amplification of the received signal which will increase the signal level at least by 30 dB.

b) Our system will allow recognition of very remote targets. The receiving part of the system will require only very moderate power and it will detect the intensity of the returned light, not the square of it as usually. Estimations show that 1000 mile recognition distance will be feasible with 200 mW optical source. This will allow usage of our systems in space for listening the ground or vibrations of other spacecrafts.

Figure 2:
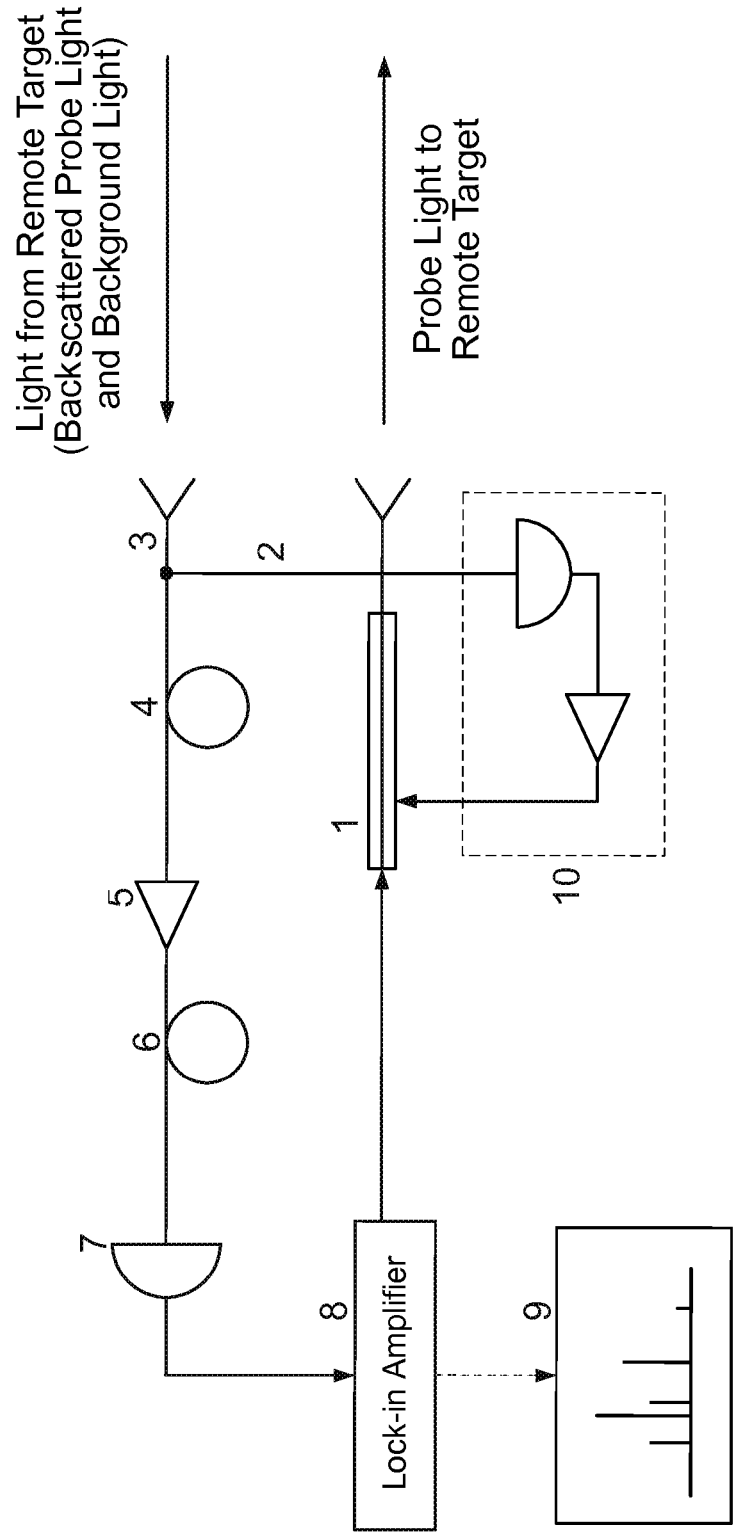
FIG. 2 shows one example of a laser sensing system.

The operational principle of the acousto-photonic system is based on laser vibrometry. Conventional remote optical vibrometry suffers from low signal-to-noise ratio resulting from unavailability of narrowband optical filters suitable for cutting out the noise from the optical signal returned from a vibrating target. We propose to develop a system that substantially increasing signal-to-noise ratio for an optical vibrometer by providing sub-kilohertz notch pre-filtering in optical domain with subsequent phase-sensitive optical signal detection (FIG. 2).

Let us discuss the system more specifically. Laser beam of moderate power illuminates the target. Reflected light ("sparkle") is received by optical antenna. Doppler shift is compensated by laser frequency detuning. The received signal is refined by a kilohertz bandpass optical filter. Output of the filter is amplified, demodulated, and sent to an acoustical spectrum analyzer and simultaneously to a loudspeaker.

Extremely narrowband optical filtering with amplification allows reducing optical power down and hiding it within regular target's night or day illumination. To ensure the sparkle is not visible when level of ambient illumination is reducing, say at dusk, the feedback circuit will adjust the emitting power constantly keeping it substantially below the illumination. This way overall power of sparkle will be at least 50 dB below natural illumination and this way undetectable by regular observer.

The last stage of the hearing setup provides with covertness even when technically advanced counter-reconnaissance systems are present. The sparkle still can be detected if the counter-system has real-time information about exact current frequency of the remote-hearing laser. In this case the covertness is compromised since opponent directly detects the sparkle. This stage allows reducing power 20 dB below the noise within acoustic band using phase sensitive technique.

To intercept the process of remote hearing at this point the opponent has to obtain real-time optical frequency of the remote-hearing laser and a current phase of the phase sensitive receiver. This does not seem realistic.

The narrowband filtering is possible because of availability of ultra-high Q crystalline whispering gallery mode (WGM) resonators. Recently we have developed a novel approach for fabrication of ultra-high Q crystalline WGM microresonators and demonstrated high contrast optical modes characterized with a kilohertz bandwidth (Q>1011) at room temperature. Theoretical simulations show that the Q-factor could be even higher if appropriate crystalline materials are chosen. The resonators are small in size and suitable for integration with other optical elements. We have also developed a computerized fabrication technique for the crystalline microresonators. The technique is based on a special diamond turning apparatus. The quality of the surface of the resonators produced with this technique is characterized by less than 0.2 nm surface roughness. The quality factor of the microresonators exceeds 107.

An optical filter can be fabricated from CaF2 or MgF2. The geometry of the resonator will be engineered in a way to obtain a so-called "single-mode" optical resonator. Such geometry significantly improves spectral resolution as well as signal-to-noise ratio. The filter will improve sensitivity of the remote hearing for a wide range of the optical frequencies scaling from 200 to 400 THz. One example of such a filer is a whispering gallery mode resonator filter.

Proposed setup will be of great interest because of its unique ability to recognize actual sound and vibration of the extremely remote targets. Deployed system will allow recognition of, for example, the particular type of U238/U235 inertial separators working at WDM facilities by vibrational spectra of the facility itself. On the battlefield it would allow recognition of false tanks on the ground or false jetfighters on the airstrip.

Proposed system will result in remote covert recognition since the weak laser carrier will be safely hidden in wideband stray light. The target under recognition will not be able to detect this process since at present time there are no methods to extract such a weak narrowband optical signal from noisy background but our proposed filtering process.

Remote optical hearing and vibrometry has been widely used, e.g. in industry, for detection of defects within operating mechanisms or recognition of their operational status. There exists a significant technical difficulty, though, in optical recognition of a weak vibration introducing modulation sidebands in the vicinity of the optical carrier. It is difficult to separate the signal from the strong ambient optical noise even using heterodyne detection scheme. We propose a novel as well as a feasible solution of the problem that will improve sensitivity of existing remote hearing devices by several orders of magnitude.

FIG. 2 shows an example of the laser sensor module 100 in FIG. 1. Laser 1 connected to antenna 2 illuminates the target. Image of the sparkle is received with antenna 3, filtered 4, amplified 5, demodulated 6 and finally detected with optical detector 7. Lock-in amplifier 8 modulates the laser's carrier providing with phase sensitive measurements. Result of remote hearing is displayed with conventional low-frequency spectrum analyzer 9. Feedback circuit 10 control laser's average power. IN operation, this system projects a single laser beam that is modulated to the target and detects the returned probe beam without using a second reference beam. The demodulation at the second optical filter in FIG. 4 performs the optical filtering and demodulation to extract the vibration signal.

FIG. 2 shows one example of a laser sensing system.

Figure 3:
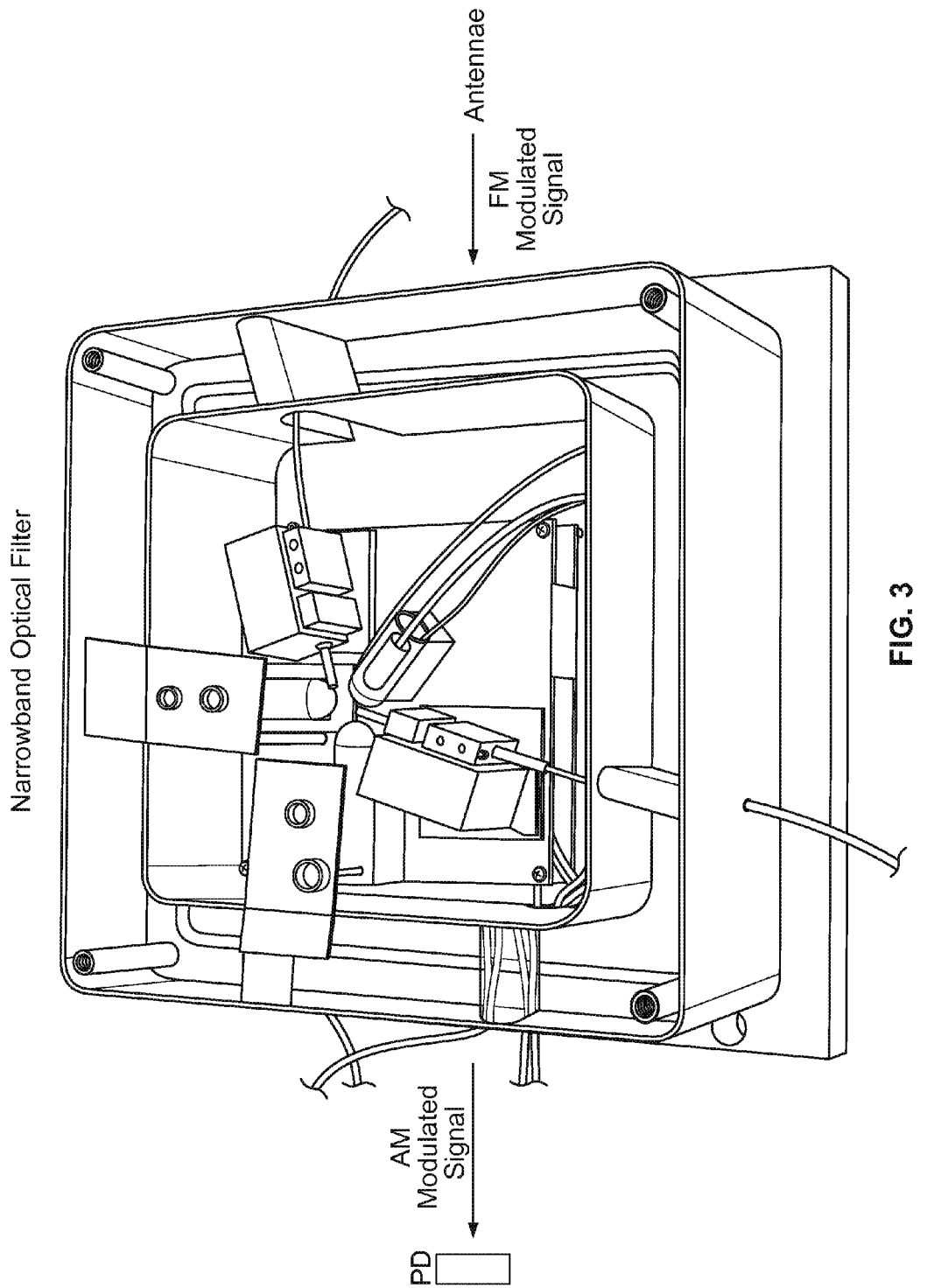
FIG. 3 shows one example of the narrow optical filter module 4 for the system in FIG. 2.

FIG. 3 shows one example of the narrow optical filter module 4 for the system in FIG. 2.

Figure 4:
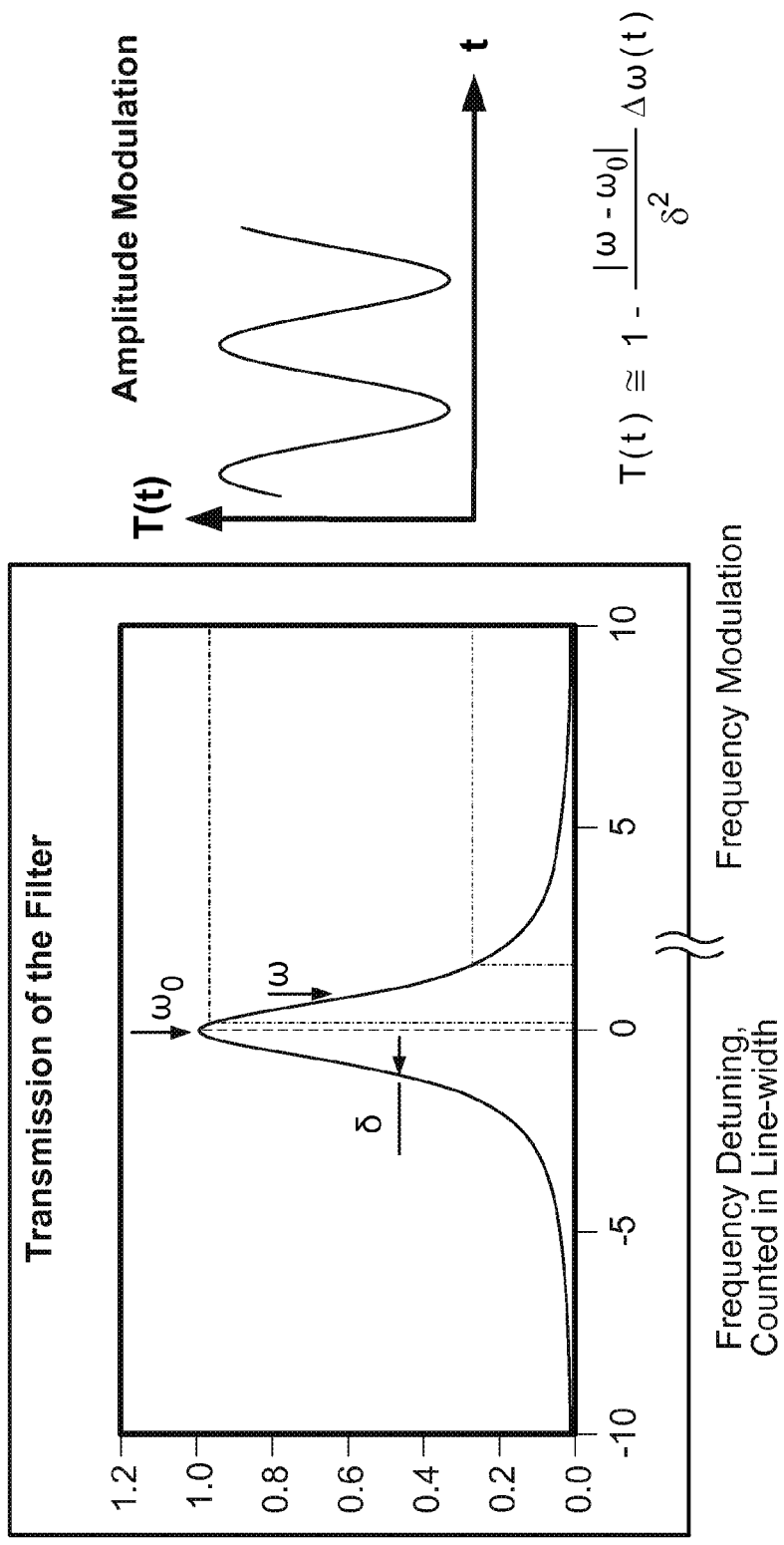
FIG. 4 shows the operation of the optical filter 6 for optical demodulation.

FIG. 4 shows the operation of the optical filter 6 for optical demodulation.

Figure 5:
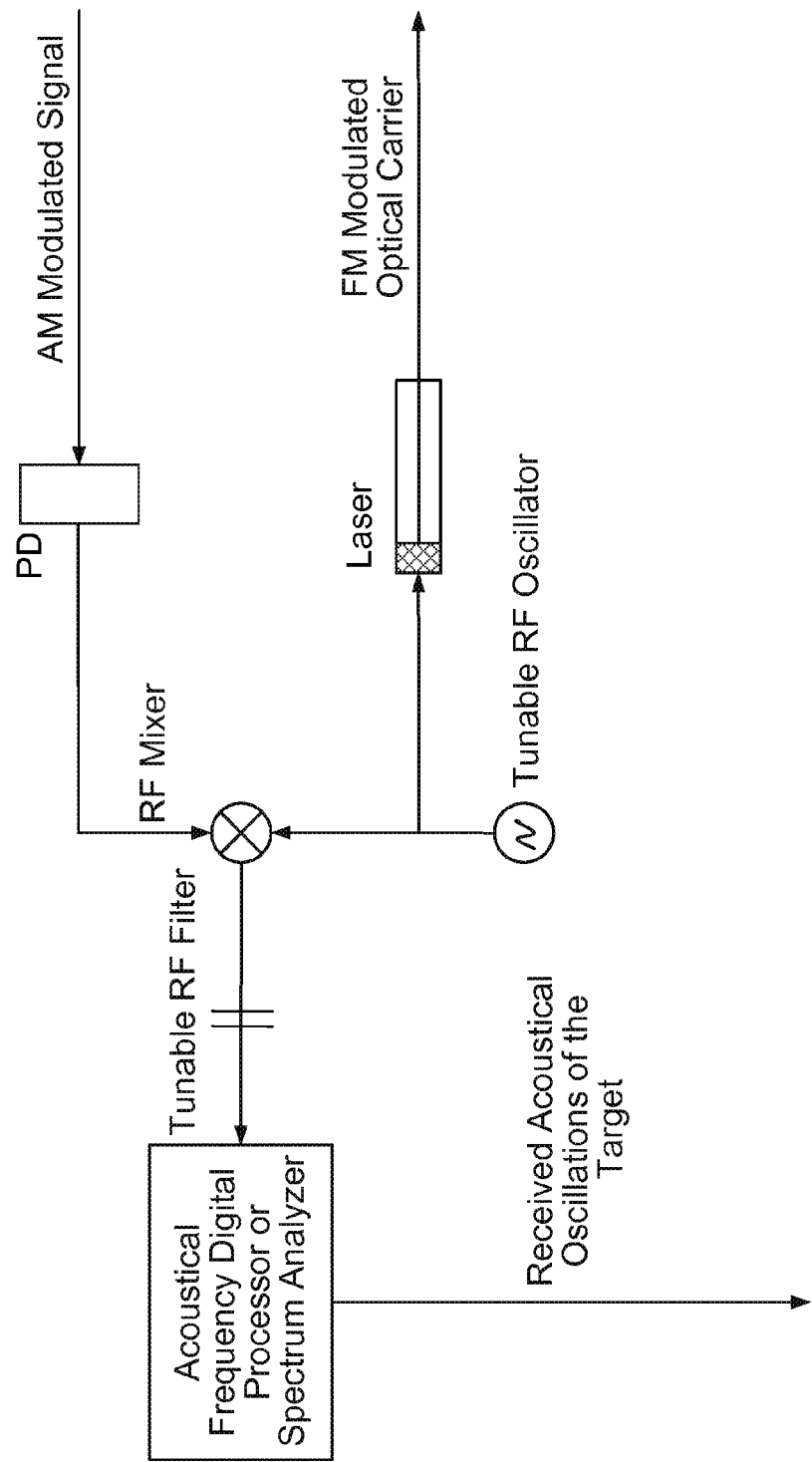
FIG. 5 shows signal processing in FIG. 2.

FIG. 5 shows signal processing in FIG. 2.

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. However, it is understood that variations, enhancements and other implementations can be made based on what is described and illustrated in this patent application.

What is claimed is:

1. A method for detecting vibrations of a target based on optical sensing, comprising:

operating a laser to produce a laser probe beam at a laser frequency and modulated at a modulation frequency onto a target;

collecting light at or near the laser to collect light from the target while the target is being illuminated by the laser probe beam through an optical receiver aperture;

using a narrow-band optical filter centered at the laser frequency to filter light collected from the optical receiver aperture to transmit light at the laser frequency while blocking light at other frequencies;

using an optical detector to convert filtered light from the narrow-band optical filter to produce a receiver electrical signal;

using a lock-in amplifier to detect and amplify the receiver electrical signal at the modulation frequency while rejecting signal components at other frequencies to produce an amplified receiver electrical signal;

processing the amplified receiver electrical signal to extract information on vibrations of the target carried by reflected laser probe beam in the collected light; and controlling optical power of the laser probe beam at the target to follow optical power of background illumination at the target.

2. The method as in claim 1, comprising:

setting the optical receiver aperture to be equal to or greater than an optical aperture of the laser probe beam at the laser.

3. The method as in claim 1, wherein:

the optical power of the laser probe beam at the target is comparable to the optical power of background illumination at the target.

4. The method as in claim 1, wherein:

the optical power of the laser probe beam at the target is controlled so that the laser probe beam at the target is covert in the background illumination at the target.

5. The method as in claim 1, comprising:

measuring optical power of the background illumination at the target; and using a feedback control in response to the measured optical power to control the laser so that the optical power of the laser probe beam at the target is covert in the background illumination at the target.

6. The method as in claim 1, comprising:

controlling the laser probe beam at the laser frequency to have a spectral linewidth of around one kilohertz.

7. A method for detecting vibrations of a target based on optical sensing, comprising:

operating a laser to produce a laser probe beam at a laser frequency and modulated at a modulation frequency onto a target;

collecting light at or near the laser to collect light from the target while the target is being illuminated by the laser probe beam through an optical receiver aperture;

using a narrow-band optical filter centered at the laser frequency to filter light collected from the optical receiver aperture to transmit light at the laser frequency while blocking light at other frequencies;

using an optical detector to convert filtered light from the narrow-band optical filter to produce a receiver electrical signal;

using a lock-in amplifier to detect and amplify the receiver electrical signal at the modulation frequency while rejecting signal components at other frequencies to produce an amplified receiver electrical signal; and processing the amplified receiver electrical signal to extract information on vibrations of the target carried by reflected laser probe beam in the collected light, wherein:

the processing of the amplified receiver electrical signal to extract information on vibrations of the target carried by reflected laser probe beam in the collected light comprises generating an acoustic signal indicating the vibrations of the target.

8. The method as in claim 7, comprising:

controlling the laser probe beam at the laser frequency to have a spectral linewidth of around one kilohertz.

9. The method as in claim 7, comprising:

setting the optical receiver aperture to be equal to or greater than an optical aperture of the laser probe beam at the laser.

10. A method for detecting vibrations of a target based on optical sensing, comprising:

directing a laser probe beam at a laser frequency, which is modulated at a modulation frequency, onto a target;

measuring optical power of the background illumination at the target;

using a feedback control in response to the measured optical power to control the optical power of the laser probe beam at the target to be covert in the background illumination at the target;

collecting light at or near the laser to collect light from the target while the target is being illuminated by the laser probe beam through an optical receiver aperture;

using a narrow-band optical filter centered at the laser frequency to filter light collected from the optical receiver aperture to transmit light at the laser frequency while blocking light at other frequencies;

converting the filtered light from the narrow-band optical filter into a receiver electrical signal;

detecting and amplifying the receiver electrical signal at the modulation frequency, while rejecting signal components at other frequencies, to produce an amplified receiver electrical signal; and extracting from the amplified receiver electrical signal an acoustic signature of the target.

11. The method as in claim 10, comprising:

setting the optical receiver aperture to be equal to or greater than an optical aperture of the laser probe beam at the laser.

12. The method as in claim 10, comprising:

controlling the laser probe beam at the laser frequency to have a spectral linewidth of around one kilohertz.

13. A device for detecting vibrations of a target based on optical sensing, comprising:

a laser module to produce a laser probe beam at a laser frequency, which is modulated at a modulation frequency;

means for directing the laser probe beam onto a target;

means for measuring background illumination at the target;

a feedback control that is responsive to the measured background illumination at the target and controls the optical power of the laser probe beam at the target to be covert in the background illumination at the target;

an antenna collecting light from the target to produce collected light;

a narrow-band optical filter centered at the laser frequency to filter the collected light from the antenna to produce filtered light at the laser frequency while blocking light at other frequencies;

an optical detector to convert the filtered light from the narrow-band optical filter into a receiver electrical signal;

an amplifier that detects and amplifies the receiver electrical signal at the modulation frequency, while rejecting signal components at other frequencies, to produce an amplified receiver electrical signal; and means for extracting from the amplified receiver electrical signal an acoustic signature of the target.

14. The device as in claim 13, wherein:

the antenna has an optical receiver aperture that is equal to or greater than an optical aperture for projecting the laser probe beam of the device onto the project.

15. The device as in claim 13, comprising:

means for controlling the laser probe beam at the laser frequency to have a spectral linewidth of around one kilohertz.

16. A device for detecting vibrations of a target based on optical sensing, comprising:

a laser module to produce a laser probe beam at a laser frequency, which is modulated at a modulation frequency;

means for directing the laser probe beam onto a target;

means for measuring background illumination at the target;

a feedback control that is responsive to the measured background illumination at the target and controls the optical power of the laser probe beam at the target to be covert in the background illumination at the target;

an antenna collecting light from the target to produce collected light;

an optical detector to convert the collected light into a receiver electrical signal;

an amplifier that detects and amplifies the receiver electrical signal at the modulation frequency, while rejecting signal components at other frequencies, to produce an amplified receiver electrical signal; and means for extracting from the amplified receiver electrical signal an acoustic signature of the target.

17. The device as in claim 16, wherein:

the antenna has an optical receiver aperture that is equal to or greater than an optical aperture for projecting the laser probe beam of the device onto the project.

18. A method for detecting vibrations of a target based on optical sensing, comprising:

directing a laser probe beam at a laser frequency, which is modulated at a modulation frequency, onto a target;

measuring optical power of the background illumination at the target;

using a feedback control in response to the measured optical power to control the optical power of the laser probe beam at the target to be covert in the background illumination at the target;

collecting light at or near the laser to collect light from the target while the target is being illuminated by the laser probe beam through an optical receiver aperture;

converting the collected light into a receiver electrical signal;

detecting and amplifying the receiver electrical signal at the modulation frequency, while rejecting signal components at other frequencies, to produce an amplified receiver electrical signal; and extracting from the amplified receiver electrical signal an acoustic signature of the target.

19. The method as in claim 18, comprising:

setting the optical receiver aperture to be equal to or greater than an optical aperture of the laser probe beam at the laser.

* * * * *